US006271307B1

(12) United States Patent
Huff et al.

(10) Patent No.: US 6,271,307 B1
(45) Date of Patent: Aug. 7, 2001

(54) USE OF POLYALKYLKENE OXIDE-CONTAINING GRAFT COPOLYMERS AS SOLUBILIZERS

(75) Inventors: Jürgen Huff, Ludwigshafen; Helmut Meffert, Mannheim; Folker Ruchatz, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/283,194

(22) Filed: Apr. 1, 1999

(30) Foreign Application Priority Data

Apr. 2, 1998 (DE) ............................................. 198 14 739

(51) Int. Cl.$^7$ ........................... C08F 291/06; A61K 7/08; A23L 3/3481
(52) U.S. Cl. ........................ 525/61; 525/194; 525/298; 525/303; 525/307; 525/309; 524/561; 424/487; 424/70.31; 426/69; 426/90
(58) Field of Search ............................ 525/61, 194, 298, 525/307, 303, 309; 524/561; 424/487, 70.31; 426/69

(56) References Cited

U.S. PATENT DOCUMENTS

| 4,846,994 | * | 7/1989 | Kud et al. | 252/174.21 |
| 5,078,994 | * | 1/1992 | Nair et al. | 424/487 |
| 5,318,719 | * | 6/1994 | Hughes et al. | 525/529 |

* cited by examiner

Primary Examiner—Nathan M. Nutter
Assistant Examiner—Olga Asinovsky
(74) Attorney, Agent, or Firm—Keil & Weinkauf

(57) ABSTRACT

The use of graft copolymers obtainable by grafting
  a) polyalkylene oxides with
  b) at least one monomer selected from the group of
    $b_1$) $C_1$–$C_{30}$-alkyl esters of monoethylenically unsaturated $C_3$–$C_8$-carboxylic acids;
    $b_2$) vinyl esters of aliphatic $C_1$–$C_{30}$-carboxylic acids;
    $b_3$) $C_1$–$C_{30}$-alkyl vinyl ethers;
    $b_4$) N—$C_1$–$C_{12}$-alkyl-substituted amides of monoethylenically unsaturated $C_3$–$C_8$-carboxylic acids;
    $b_5$) N,N—$C_1$–$C_{12}$-dialkyl-substituted amides of monoethylenically unsaturated $C_3$–$C_8$-carboxylic acids as solubilizer.

12 Claims, No Drawings

USE OF POLYALKYLKENE OXIDE-CONTAINING GRAFT COPOLYMERS AS SOLUBILIZERS

The invention relates to the use of polyalkylene oxide-containing graft copolymers as solubilizers.

The solubilization of hydrophobic substances has become of very great practical importance in the production of homogeneous pharmaceutical or cosmetic preparations.

Solubilization means improving the solubility by using amphiphilic compounds able to convert substances which are insoluble or are of low solubility in water into clear, or at most opalescent, aqueous solutions without this involving an alteration in the chemical structure of these substances.

The solubilisates which are produced contain the substance which is insoluble or of low solubility in water dissolved in the aggregates of molecules of the amphiphilic compounds formed in the aqueous solution, which are called micelles. The resulting solutions are stable single-phase systems which appear optically clear or opalescent and can be produced without input of energy.

Solubilizers are able, for example, to improve the appearance of cosmetic formulations and of food products by making the formulations transparent. In addition, in the case of pharmaceutical preparations, the bioavailability and thus the effect of drugs can be increased by using solubilizers.

The solubilizers employed for pharmaceutical substances and cosmetic ingredients are mainly the following products:
  ethoxylated (hydrogenated) castor oil (e.g. Cremophor® types supplied by BASF);
  ethoxylated sorbitan fatty acid esters (e.g. Tween® types supplied by ICI);
  ethoxylated hydroxystearic acid (e.g. Solutol® HS 15 supplied by BASF).

However, the solubilizers described above and employed to date have a number of technical disadvantages on use.

Thus, for example, parenteral administration thereof is associated with release of histamine and a resulting fall in blood pressure (Lorenz et al., Agents and Actions, Vol. 12, 1/2, 1982).

Known solubilizers have only a low solubilizing action for some medicinal substances of low solubility, such as clotrimazole.

Surface-active compounds often have high hemolytic activity which prevents use in the pharmaceuticals sector, especially in parenteral products.

EP-A-0 219 048 describes the use of graft copolymers of polyalkylene oxides and vinyl acetate as antiredeposition agents in the washing and after-treatment of synthetic fiber-containing textile materials.

It is an object of the present invention to provide novel solubilizers without the abovementioned disadvantages for pharmaceutical, cosmetic and foodstuff applications.

We have found that this object is achieved by using graft copolymers obtained by grafting
  a) polyalkylene oxides with
  b) at least one monomer selected from the group of
    $b_1$) $C_1$–$C_{30}$-alkyl esters of monoethylenically unsaturated $C_3$–$C_8$-carboxylic acids;
    $b_2$) vinyl esters of aliphatic $C_1$–$C_{30}$-carboxylic acids;
    $b_3$) $C_1$–$C_{30}$-alkyl vinyl ethers;
    $b_4$) N—$C_1$–$C_{30}$-alkyl-substituted amides of monoethylenically unsaturated $C_3$–$C_8$-carboxylic acids;
    $b_5$) N,N—$C_{-C30}$-dialkyl-substituted amides of monoethylenically unsaturated $C_3$–$C_8$-carboxylic acids as solubilizer.

It is possible to use as grafting base a) in general polyalkylene oxides, in particular those having an average molecular weight of from 300 to 100,000 g/mol and based on ethylene oxide, propylene oxide and/or butylene oxide.

Homopolymers of ethylene oxide or copolymers with an ethylene oxide content of from 40 to 99% by weight are preferably used. Thus, for the ethylene oxide polymers which are preferably to be employed, the content of ethylene oxide units is from 40 to 100 mol %. Suitable comonomers for these copolymers are propylene oxide, butylene oxide and/or isobutylene oxide. Suitable examples are copolymers of ethylene oxide and propylene oxide, copolymers of ethylene oxide and butylene oxide, and copolymers of ethylene oxide, propylene oxide and at least one butylene oxide. The ethylene oxide content in the copolymers is preferably from 40 to 99 mol %, the propylene oxide content is from 1 to 60 mol %, and the butylene oxide content in the copolymers is from 1 to 30 mol %. It is possible to use not only straight-chain but also branched homo- or copolymers as grafting base.

Branched copolymers can be produced by, for example, adding ethylene oxide and, where appropriate, propylene oxide and/or butylene oxides onto polyhydric low molecular weight alcohols, e.g. trimethylolpropane, pentoses or hexoses. The alkylene oxide units can be randomly distributed in the polymer or be present in the form of blocks.

The component a) which is particularly preferably used comprises polyethylene oxides with a human average molecular weight of from 500 to 20,000, in particular 800 to 10,000 g/mol.

However, it is also possible to use polyesters of polyalkylene oxides and aliphatic or aromatic dicarboxylic acids, e.g. oxalic acid, succinic acid or adipic acid, with molecular weights of from 1500 to 25,000, described in EP-A-0 743 962, as grafting base.

As component b) for grafting onto the polyalkylene oxides, mention may be made of the following copolymerizable monomers:

$C_1$–$C_{30}$-alkyl esters of monoethylenically unsaturated carboxylic acids with 3 to 8 C atoms, e.g. acrylic acid, methacrylic acid, dimethylacrylic acid, ethacrylic acid, maleic acid, citraconic acid, methylenemalonic acid, allylacetic acid, vinylacetic acid, crotonic acid, fumaric acid, mesaconic acid and itaconic acid.

$C_1$–$C_{30}$-Alcohols, preferably $C_1$–$C_{12}$-alcohols, particularly preferably $C_1$–$C_6$-alcohols may be mentioned as alcohol component in the abovementioned esters.

The monoethylenically unsaturated carboxylic acids preferably used are acrylic acid, methacrylic acid, maleic acid or mixtures of said carboxylic acids.

Particularly important in this connection are the acrylic, methacrylic and maleic esters with alcohols having a chain length of from 1 to 12, preferably 1 to 6, carbon atoms.

Particular mention may be made here of: methyl acrylate, ethyl acrylate, n-propyl acrylate, isopropyl acrylate, n-butyl acrylate, 1-methylpropyl acrylate, 2-methylpropyl acrylate, n-hexyl acrylate, n-heptyl acrylate, n-octyl acrylate, 2-ethylhexyl acrylate, nonyl acrylate, decyl acrylate, lauryl acrylate, methyl methacrylate, ethyl methacrylate, n-propyl methacrylate, isopropyl methacrylate, n-butyl methacrylate, 1-methylpropyl methacrylate, 2-methylpropyl methacrylate, n-hexyl methacrylate, n-heptyl methacrylate, n-octyl methacrylate, 2-ethylhexyl methacrylate, nonyl methacrylate, decyl methacrylate and lauryl methacrylate.

It is possible to employ as further component b) vinyl esters of aliphatic, saturated or unsaturated $C_1$–$C_{30}$-carboxylic acids, e.g. formic acid, acetic acid, propionic acid, butyric acid, valeric acid, isovaleric acid, caproic acid, caprylic acid, capric acid, undecylenic acid, lauric acid, myristic acid, palmitic acid, palmitoleic acid, stearic acid, oleic acid, arachic acid, behenic acid, lignoceric acid, cerotic acid and melissic acid.

Preference is given to using vinyl esters of the abovementioned $C_1$–$C_{12}$-carboxylic acids, in particular $C_1$–$C_6$-carboxylic acids.

It is also possible for $C_1$–$C_{30}$-alkyl vinyl ethers, preferably $C_1$–$C_{12}$-alkyl vinyl ethers, particularly preferably $C_1$–$C_6$-alkyl vinyl ethers, to be used for the graft copolymerization.

Alkyl radicals which may be mentioned as preferred in the vinyl ethers are branched or unbranched $C_1$–$C_6$-alkyl chains such as methyl, ethyl, n-propyl, isopropyl, n-butyl, 2-methylpropyl, 1-methylpropyl, n-pentyl and n-hexyl.

It is also possible to use as component b) N—$C_1$–$C_{30}$-alkyl- or N,N—$C_1$–$C_{30}$-dialkyl-substituted amides of monoethylenically unsaturated $C_3$–$C_8$-carboxylic acids, where the alkyl radicals are aliphatic or cycloaliphatic alkyl radicals having 1 to 30, preferably 1 to 12, particularly preferably 1 to 6, carbon atoms.

The monoethylenically unsaturated carboxylic acids having 3 to 8 C atoms likewise mean the abovementioned acids, preferably acrylic acid, methacrylic acid, dimethylacrylic acid, ethacrylic acid, maleic acid, citraconic acid, methylenemalonic acid, allylacetic acid, vinylacetic acid, crotonic acid, fumaric acid, mesaconic acid and itaconic acid.

It is likewise particularly preferred to use acrylic acid, methacrylic acid, maleic acid or mixtures of said carboxylic acids from this group of monomers.

Preferred amidated comonomers are, for example, N-methylacrylamide, N-methylmethacrylamide, N-ethylacrylamide, N-ethylmethacrylamide, N-n-propylacrylamide, N-n-propylmethacrylamide, N-isopropylacrylamide, N-isopropylmethacrylamide, N-n-butylacrylamide, N-n-butylmethacrylamide, N-1-methylpropylacrylamide, N-1-methylpropylmethacrylamide, N-2-methylpropylacrylamide, N-2-methylpropylmethacrylamide, N-n-hexylacrylamide, N-n-hexylmethacrylamide, N-n-heptylacrylamide, N-n-heptylmethacrylamide, N-n-octylacrylamide, N-n-octylmethacrylamide, N-2-ethylhexylacrylamide, N-2-ethylhexylmethacrylamide, N-nonylacrylamide, N-nonylmethacrylamide, N-decylacrylamide, N-decylmethacrylamide, N-laurylacrylamide, N-laurylmethacrylamide.

It is, of course, also possible for mixtures of each of the group b) monomers to be used for the graft copolymerization.

The hydrophobic monomers may also be employed in a mixture with one or more hydrophilic comonomers. Those which can be used are ethylenically unsaturated carboxylic acids such as acrylic acid, methacrylic acid, maleic acid, fumaric acid, itaconic acid, aconitic acid, as well as N-vinylpyrrolidone, N-vinylimidazole or N-vinylcaprolactam.

The graft copolymers used according to the invention have an average molecular weight of from 1000 to 30,000 g/mol, preferably 2000 to 20,000 g/mol, particularly preferably 3000 to 8000 g/mol.

The graft copolymers have K values of at least 7, preferably 10 to 30, particularly preferably 10–25. The K values are determined by the method of H. Fikentscher, Cellulose-Chemie, volume 13, 58 to 64 and 71 to 74 (1932) in acetone at 25° C. and with polymer concentrations between 0.1% and 5%, depending on the K value range.

The graft copolymers are produced by grafting the suitable polyalkylene oxides of component (a) with the monomers of component (b) in the presence of free radical initiators or by exposure to high-energy radiation, by which is also meant exposure to high-energy electrons.

The procedure for this can be such that the polyalkylene oxide is dissolved in at least one group (b) monomer and, after addition of a polymerization initiator, the mixture is polymerized to completion. The graft copolymerization can also be carried out semibatchwise by initially mixing part, e.g. 10%, of the mixture which is to be polymerized and consists of polyalkylene oxide, at least one group (b) monomer and initiator, heating the mixture to the polymerization temperature and, after the polymerization has started, adding the remainder of the mixture to be polymerized as the polymerization progresses. The graft copolymers can also be obtained by introducing the polyalkylene oxides of group (a) into a reactor, heating to the polymerization temperature, and adding, either all at once, batchwise or, preferably, continuously, at least one group (b) monomer and polymerization initiator, and polymerizing.

The (a):(b) component ratio by weight is from 1:0.2 to 1:10 and is preferably in the range from 1:0.5 to 1:5.

Particularly suitable polymerization initiators are organic peroxides such as diacetyl peroxide, dibenzoyl peroxide, succinyl peroxide, di-tert-butyl peroxide, tert-butyl perbenzoate, tert-butyl perpivalate, tert-butyl permaleate, cumene hydroperoxide, diisopropyl peroxydicarbonate, bis (o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, and mixtures of said initiators, redox initiators and azo initiators.

The amounts used of initiator or initiator mixtures are between 0.01 and 10% by weight, preferably between 0.3 and 5% by weight, based on the monomer employed.

The graft copolymerization is carried out at temperatures in the range from 50 to 200° C., preferably in the range from 60 to 140° C., particularly preferably in the range from 70 to 110° C. It is normally carried out under atmospheric pressure, but can also take place under reduced or elevated pressure, preferably between 1 and 5 bar.

If required, the graft copolymerization described above can also be carried out in a solvent. Examples of suitable solvents are alcohols such as methanol, ethanol, n-propanol, isopropanol, n-butanol, sec-butanol, tert-butanol, n-hexanol and cyclohexanol, and glycols such as ethylene glycol, propylene glycol and butylene glycol, and the methyl or ethyl ethers of dihydric alcohols, diethylene glycol, triethylene glycol, glycerol and dioxane. The graft copolymerization can also be carried out in water as solvent. In this case, a solution is initially present and is more or less readily soluble in water depending on the amount of added monomers of component b). In order to dissolve products which are insoluble in water and may be produced during the polymerization, it is possible, for example, to add organic solvents such as monohydric alcohols with 1 to 3 carbon atoms, acetone or dimethylformamide. However, the procedure for graft copolymerization in water can also be such that the graft copolymers which are insoluble in water are converted into a fine-particle dispersion by adding conventional emulsifiers or protective colloids, e.g. polyvinyl alcohol.

Examples of emulsifiers which are used are ionic or nonionic surfactants whose HLB is in the range from 3 to 13. For the definition of the HLB, reference is made to the publication by W.C. Griffin, J. Soc. Cosmetic Chem., volume 5, 249 (1954).

The amount of surfactants is from 0.1 to 5% by weight, based on the graft copolymer. Solutions or dispersions of the graft copolymers are obtained on use of water as solvent. Where solutions of the graft copolymer are produced in an organic solvent or in mixtures of an organic solvent and water, from 5 to 200, preferably 10 to 100, parts by weight of the organic solvent or mixture of solvents are used per 100 parts by weight of the graft copolymer.

Applications

The present invention makes amphiphilic compounds available for use as solubilizers for pharmaceutical and cosmetic preparations and for food products. They have the property of solubilizing pharmaceutical and cosmetic active ingredients of low solubility, food supplements of low solubility, for example vitamins and carotenoids, but also active ingredients of low solubility for use in crop protection agents, and veterinary medical active ingredients.

The claimed compounds have surprisingly been found to have a good solubilizing capacity for pharmaceutical and cosmetic active ingredients. In addition, the claimed compounds provide applications distinguished by a very low rate of hemolysis and tolerability without side effects after parenteral, oral and topical administration onto skin and mucous membranes. The compounds have, in particular, no side effects due to interactions with membranes of blood corpuscles. Parenteral administration is followed by only slight or no histamine release. The solubilizers can, owing to their low molecular weight, be excreted through the kidneys.

Solubilizers for Cosmetics

The graft copolymers used according to the invention can be employed as solubilizers in cosmetic formulations. For example, they are suitable as solubilizers for cosmetic oils. They have a good solubilizing capacity for fats and oils such as arachis oil, jojoba oil, coconut oil, almond oil, olive oil, palm oil, castor oil, soybean oil or wheat germ oil or for essential oils such as mountain pine oil, lavender oil, rosemary oil, pine needle oil, fir needle oil, eucalyptus oil, peppermint oil, sage oil, bergamot oil, turpentine oil, melissa oil, juniper oil, lemon oil, aniseed oil, cardamom oil, camphor oil etc. or for mixtures of these oils.

The polymers used according to the invention can also be used as solubilizers for UV absorbers which are insoluble or of low solubility in water, such as 2-hydroxy-4-methoxybenzophenone (Uvinul® M 40, supplied by BASF), 2,2',4,4'-tetrahydroxybenzophenone (Uvinul® D 50), 2,2'-dihydroxy-4,4'-dimethoxybenzophenone (Uvinul® D49), 2,4-dihydroxybenzophenone (Uvinul® 400), 2-ethylhexyl 2-cyano-3,3-diphenylacrylate (Uvinul® N 539), 2,4,6-tris (p-2-ethylhexoxycarbonylanilino)-1,3,5-triazine (Uvinul® T 150), 3-(4-methoxybenzylidene)camphor (Eusolex® 6300, supplied by Merck), 2-ethylhexyl N,N-dimethyl-4-aminobenzoate (Eusolex® 6007), 3,3,5-trimethylcyclohexyl salicylate, 4-isopropyldibenzoylmethane (Eusolex® 8020), 2-ethylhexyl p-methoxycinnamate and isoamyl p-methoxycinnamate, and mixtures thereof.

The present invention therefore also relates to cosmetic preparations which comprise at least one of the graft copolymers of the composition mentioned at the outset and used according to the invention as solubilizers. Preferred preparations are those comprising not only the solubilizer but also one or more cosmetic active ingredients of low solubility, for example the abovementioned oils or UV absorbers.

These formulations comprise solubilisates based on water or water/alcohol. The solubilizers according to the invention are employed in the ratio of from 0.2:1 to 20:1, preferably 1:1 to 15:1, particularly preferably 2:1 to 12:1, to the cosmetic active ingredient of low solubility.

The content of solubilizer used according to the invention in the cosmetic preparation is in the range from 1 to 50% by weight, preferably 3 to 40% by weight, particularly preferably 5 to 30% by weight, depending on the active ingredient.

It is also possible to add further ancillary substances to this formulation, for example nonionic, cationic or anionic surfactants such as alkyl polyglycosides, fatty alcohol sulfates, fatty alcohol ether sulfates, alkanesulfonates, fatty alcohol ethoxylates, fatty alcohol phosphates, alkyl betaines, sorbitan esters, POE-sorbitan esters, sugar fatty acid esters, fatty acid polyglycerol esters, fatty acid partial glycerides, fatty acid carboxylates, fatty alcohol sulfosuccinates, fatty acid sarcosinates, fatty acid isethionates, fatty acid taurates, citric esters, silicone copolymers, fatty acid polyglycol esters, fatty amides, fatty alkanolamides, quaternary ammonium compounds, alkylphenol ethoxylates, fatty amine ethoxylates, cosolvents such as ethylene glycol, propylene glycol, glycerol etc.

Further ingredients which can be added are natural or synthetic compounds, e.g. lanolin derivatives, cholesterol derivatives, isopropyl myristate, isopropyl palmitate, electrolytes, dyes, preservatives, acids (e.g. lactic acid, citric acid).

These formulations are used, for example, in bath additives such as bath oils, shaving lotions, face lotions, mouthwashes, hair lotions, eau de Cologne, eau de toilette and in sunscreens.

Description of the Solubilization Method

The graft copolymers used according to the invention can be employed as 100% pure substance or, preferably, as aqueous solution to produce the solubilisates for cosmetic formulations.

Normally, the cosmetic active ingredient of low solubility to be used is dissolved in a melt of the solubilizer and then, while stirring continuously, demineralized water is added.

However, it is also possible to dissolve the solubilizer in water and mix it vigorously with the particular cosmetic active ingredient of low solubility to be used.

Solubilizers for Pharmaceutical Applications

The graft copolymers used according to the invention are equally suitable for use as solubilizer in pharmaceutical preparations of any type which may comprise one or more medicinal substances which are insoluble or of low solubility in water, and vitamins and/or carotenoids. These are, in particular, aqueous solutions or solubilisates for oral or, particularly preferably, for parenteral administration, e.g. solutions for administration by intravenous, intramuscular or subcutaneous or intraperitoneal injection.

The graft copolymers are also suitable for use in oral dosage forms such as tablets, capsules, powders and solutions. In these they may increase the bioavailability of the medicinal substance of low solubility.

It is possible to employ for parenteral administration not only solubilisates but also emulsions, for example lipid emulsions. The graft copolymers used according to the invention are also suitable for processing a medicinal substance of low solubility for this purpose.

Pharmaceutical formulations of the abovementioned type can be obtained by processing the graft copolymers with pharmaceutical active ingredients by conventional methods and employing known and novel active ingredients.

The preparation according to the invention may additionally contain pharmaceutical ancillary substances and/or diluents. Ancillary substances which are particularly mentioned are cosolvents, antioxidants and preservatives.

The pharmaceutical active ingredients used are substances which are insoluble or of low solubility in water. According to DAB 9 (German Pharmacopeia), the solubility of pharmaceutical active ingredients is categorized as follows: sparingly soluble (soluble in 30 to 100 parts of solvent); slightly soluble (soluble in 100 to 1000 parts of solvent); very slightly soluble (soluble in 1000 to 10,000 parts of solvent); practically insoluble (soluble in more than 10,000 parts of solvent). The active ingredients can moreover be derived from any range of indications.

Examples which may be mentioned here are benzodiazepines, antihypertensives, vitamins, cytostatics—especially taxol, anesthetics, neuroleptics, antidepressants, antibiotics, antimycotics, fungicides, chemotherapeutics, urologicals, platelet aggregation inhibitors, sulfonamides, spasmolytics, hormones, immunoglobulins, sera, thyroid therapeutics, psychopharmaceuticals, antiparkinson agents and other antihyperkinetics, ophthalmologicals, neuropathy products, calcium metabolism regulators, muscle relaxants, anesthetics, lipid lowering agents, hepatotherapeutics, coronary agents, cardiac agents, immunotherapeutics, regulatory peptides and their inhibitors, hypnotics, sedatives, gynecologicals, antigout agents, fibrinolytics, enzyme products and transport proteins, enzyme inhibitors, emetics, blood flow stimulators, diuretics, diagnostic aids, corticoids, cholinergics, biliary therapeutics, antiasthmatics, bronchospasmolytics, beta receptor blockers, calcium channel blockers, ACE inhibitors, antiarteriosclerotics, antiinflammatory agents, anticoagulants, antihypotensives, antihypoglycemics, antifibrinolytics, antiepileptics, antiemetics, antidotes, antidiabetics, antiarrhythmics, antianemics, antiallergics, anthelmintics, analgesics, analeptics, aldosterone antagonists, and slimming products.

The graft copolymers can be used as solubilizers for example by dispersing or dissolving the active ingredient in the solubilizer, where appropriate with heating, and mixing with water while stirring.

Another production variant is to dissolve the solubilizer in the aqueous phase, where appropriate with gentle heating, and then to dissolve the active ingredient in the aqueous solubilizer solution. It is likewise possible to dissolve solubilizer and active ingredient simultaneously in the aqueous phase.

It is also possible to dissolve the solubilizer together with the active ingredient in an organic solvent, for example ethanol, isopropanol or acetone, where appropriate with heating, and to mix this solution cautiously with water, which has likewise been heated. Removal of the organic solvent by distillation results in a clear or opalescent active ingredient solubilisate.

The invention also relates to pharmaceutical preparations which comprise at least one of the graft copolymers used according to the invention as solubilizer. Preferred preparations are those which comprise not only the solubilizer but also a pharmaceutical active ingredient which is insoluble or of low solubility in water, for example from the abovementioned areas of indication.

Particularly preferred pharmaceutical preparations from those mentioned above are formulations which can be administered parenterally.

The content of solubilizer used according to the invention in the pharmaceutical preparation is in the range from 1 to 50% by weight, preferably 3 to 40% by weight, particularly preferably 5 to 30% by weight, depending on the active ingredient.

Solubilizers for Food Products

Besides use in cosmetics and pharmacy, the graft copolymers used according to the invention are also suitable as solubilizers in the food sector for nutritional substances, auxiliary or additives which are insoluble or of low solubility in water, e.g. fat-soluble vitamins or carotenoids. Examples which may be mentioned are clear beverages colored with carotenoids.

Solubilizers for Crop Protection Products

Agrochemical applications of the graft copolymers as solubilizers may comprise, inter alia, formulations which contain pesticides, herbicides, fungicides or insecticides, especially including crop protection products employed by spraying or watering.

The production and use of the graft copolymers according to the invention is explained in detail in the following examples.

EXAMPLES 1–3

Graft Copolymerization of Vinyl Acetate with Polyethylene Glycol

The graft copolymers were produced as disclosed in DE-C-10 77 430 by polymerizing 70 parts by weight of vinyl acetate in each case onto the polyethylene oxide indicated in Table 1 (30 parts by weight) at 105° C. using 2.25% by weight, based on the monomers employed in the graft copolymerization, of dibenzoyl peroxide.

TABLE 1

| Example | Parts by weight of vinyl acetate | Polyethylene oxide Mw | L value (1% in acetone) | Molecular weight (Mw) |
| --- | --- | --- | --- | --- |
| 1 | 70 | 6000 | 21 | 20,000 |
| 2 | 70 | 4000 | 21 | 20,000 |
| 3 | 70 | 1500 | 15 | 10,000 |

Cosmetic Formulations

EXAMPLE 4

6 g of solubilizer prepared as in Examples 1 and 2 were thoroughly mixed with 1 g of each of the essential oils or perfume oils listed in Table 2 using a magnetic stirrer. With continuous stirring, demineralized water was slowly added from a burette to make up to 100 g. The resulting formulations had the following composition:

1% by weight of essential or cosmetic oil, 6% by weight of solubilizer, 93% by weight of water.

TABLE 2

| Solubilizer | Essential oil | Appearance of the formulation |
| --- | --- | --- |
| Example 1 | Pine needle oil | opaline solubilisate |
| Example 1 | Rosemary oil | opaline solubilisate |
| Example 1 | Lavender oil | clear solubilisate |

TABLE 2-continued

| Solubilizer | Essential oil | Appearance of the formulation |
|---|---|---|
| Example 1 | Drom "Minos" aftershave | opaline solubilisate |
| Example 2 | Mountain pine oil | clear solubilisate |
| Example 2 | Lavender oil | opaline solubilisate |

EXAMPLE 5

Sunscreen 25 g of polymer from Example 2 were melted at about 60° C., and 2.5 g of Uvinul® T 150 (from BASF) were dissolved in the melt. A mixture of 62.5 g of double-distilled water and 10 g of glycerol, which had been heated to 60° C., was then cautiously added dropwise with stirring. A clear solution resulted and was, after cooling to room temperature, introduced into a suitable container.

Pharmaceutical Formulations

EXAMPLE 6

Diazepam Injection Solution 400 mg of polymer from Example 2 were dissolved in 1578 mg of double-distilled water. Then 10 mg of diazepam were added to the solubilizer solution, which was stirred until the medicinal substance had dissolved. 2 mg of sodium disulfite and 10 mg of benzyl alcohol were added to the solution as preservatives, and it was sterilized by filtration and dispensed into vials by conventional methods.

EXAMPLE 7

17β-Estradiol Gelatin Capsules 100 mg of 17β-estradiol were mixed with 10 g of polymer of Example 2, 80 g of molten PEG 6000 and 10 g of ethanol and then dispensed directly in liquid form into capsules.

EXAMPLE 8

Oral Ciclosporin Formulation (liquid-filled Capsule)

100 g of ciclosporin A were dissolved in 770 g of polymer of Example 2, 100 ml of ethanol and 75 ml of propylene glycol, and the clear viscous solution was then dispensed into capsules. Infinite dilution of this solution with water was possible.

EXAMPLE 9

Diazepam Emulsion for Parenteral Administration 160 g of polymer of Example 2 were dissolved in 660 g of double-distilled water. 10 g of diazepam were dispersed or dissolved in a 1:1 mixture of soybean oil and Miglyol oil (oil phase amounted to 200 g). 10 g of soybean lecithin were also employed and were dissolved in the oil phase. The two phases were predispersed and then emulsified by high-pressure homogenization.

EXAMPLE 10

17β-Estradiol Tablet 10 g of 17β-estradiol were melted with 50 g of polymer of Example 2. The melt was taken up on 940 g of Ludipress® (supplied by BASF). The granules were mixed with 0.5 g of Mg stearate and the mixture was then tableted.

EXAMPLE 11

Diazepam-containing Powder

Diazepam and the polymer of Example 2 as solubilizer were dissolved in an organic solvent, e.g. ethanol. Then an excipient, e.g. sorbitol, was added and likewise dissolved. The solvent was then removed, and the mixture was dried in vacuo.

EXAMPLE 12

Solubilizing Effect Taking the Example of 17β-estradiol, Nifedipine and Clotrimazole 17β-Estradiol, nifedipine and clotrimazole were each added in excess to a melt of the polymers used according to the invention at 65° C. The aqueous phase was then added and the mixture was stirred slowly until equilibrium was established. The excess solid was filtered off, and the content of dissolved active ingredient in the filtrate was determined (see Table 3).

TABLE 3

| | Solubilization [% by weight] | | |
|---|---|---|---|
| Copolymer | 17β-Estradiol | Nifedipine | Clotrimazole |
| Polymer (Example 1) | 0.12 | 0.41 | 0.28 |
| Polymer (Example 2) | 0.11 | 0.43 | 0.29 |
| Polymer (Example 3) | 0.15 | 0.39 | — |
| Comparison: | | | |
| Phosphate buffer, pH 7.0 | 0.0 | | 0.0 |
| Tween ® 80 | 0.09 | 0.28 | 0.03 |
| Cremophor ® EL | 0.06 | 0.27 | 0.01 |

EXAMPLE 13

Determination of the Hemolytic Activity in the RBC Test

The hemolytic activity of the claimed compounds was tested in an RBC (Red Blood Cell) test on rabbit erythrocytes (see Table 4). The incubation time was 60 min at room temperature.

TABLE 4

| Compound | Hemolysis of the 1% strength solutions in phosphate buffer |
|---|---|
| Phosphate buffer pH 7.0 | none |
| Sorbitan fatty acid ester (Tween ® 80) | none |
| Ethoxylated castor oil (Cremophor ® EL) | none |
| Example 1 | none |
| Example 2 | none |
| Example 3 | none |

EXAMPLE 14

Tolerability in Dogs

The release of histamine into the blood was followed after intravenous injection of a 5% strength aqueous solution of the claimed compounds in dogs (Table 5).

TABLE 5

| Compound | 5 min before administration | 5 min after administration | 15 min after administration |
| --- | --- | --- | --- |
| Sorbitan fatty acid ester (Tween ® 80) | 3*) | 14,142 | 58,065 |
| Solutol ® HS 15 | 5 | 138 | 220 |
| Polymer of Example 2 | 5 | 312 | 104 |

*)The stated numbers represent the blood levels of histamine in ng/ml.

We claim:

1. A pharmaceutical preparation comprising at least one graft copolymer consisting essentially of the copolymer prepared by grafting
   a) a polyalkylene oxide with
   b) at least one monomer selected from the group of
      $b_1$) $C_1$–$C_{30}$-alkyl esters of monoethylenically unsaturated $C_3$–$C_{30}$-carboxylic acids:
      $b_2$) vinyl esters of aliphatic $C_1$–$C_{30}$-carboxylic acids;
      $b_3$) $C_1$–$C_{30}$-alkyl vinyl ethers;
      $b_4$) N—$C_1$–$C_{30}$-alkyl-substituted amides of monoethylenically unsaturated $C_3$–$C_8$-carboxylic acids; and
      $b_5$) N,N—$C_1$–$C_{30}$-dialkyl-substituted amides of monoethylenically unsaturated $C_3$–$C_8$-carboxylic acids as solubilizer.

2. A cosmetic preparation comprising at least one graft copolymer consisting essential of the copolymer prepared by grafting
   a) a polyalkylene oxide with
   b) at least one monomer selected from the group of
      $b_1$) $C_1$–$C_{30}$-alkyl esters of monoethylenically unsaturated $C_3$–$C_8$-carboxylic acids:
      $b_2$) vinyl esters of aliphatic $C_1$–$C_{30}$-carboxylic acids;
      $b_3$) $C_1$–$C_{30}$-alkyl vinyl ethers;
      $b_4$) N—$C_1$–$C_{30}$-alkyl-substituted amides of monoethylenically unsaturated $C_3$–$C_8$-carboxylic acids; and
      $b_5$) N,N—$C_1$–$C_{30}$-dialkyl-substituted amides of monoethylenically unsaturated $C_3$–$C_8$-carboxylic acids as solubilizer.

3. A food product comprising at least one graft copolymer consisting essentially of the copolymers prepared by grafting
   a) a polyalkylene oxide with
   b) at least one monomer selected from the group of
      $b_1$) $C_1$–$C_{30}$-alkyl esters of monoethylenically unsaturated $C_3$–$C_8$-carboxylic acids;
      $b_2$) vinyl esters of aliphatic $C_1$–$C_{30}$-carboxylic acids;
      $b_3$) $C_1$–$C_{30}$-alkyl vinyl ethers;
      $b_4$) N—$C_1$–$C_{30}$-alkyl-substituted amides of monoethylenically unsaturated $C_3$–$C_8$-carboxylic acids; and
      $b_5$) N,N—$C_1$–$C_{30}$-dialkyl-substituted amides of monoethylenically unsaturated $C_3$–$C_8$-carboxylic acids as solubilizer.

4. The pharmaceutical preparation of claim 1, wherein the polyalkylene oxide has a number average molecular weight of from 300 to 100,000 and is based on ethylene oxide, propylene oxide and/or butylene oxide.

5. The pharmaceutical preparation of claim 1, wherein the polyalkylene oxide has a number average molecular weight of from 500 to 20,000 and is based on ethylene oxide and/or propylene oxide.

6. The pharmaceutical preparation of claim 1, wherein the graft copolymer has a number average molecular weight of from 1000 to 30,000 g/mol.

7. The cosmetic preparation of claim 2, wherein the polyalkylene oxide has a number average molecular weight of from 300 to 100,000 and is based on ethylene oxide, propylene oxide and/or butylene oxide.

8. The cosmetic preparation of claim 2, wherein the polyalkylene oxide has a number average molecular weight of from 500 to 20,000 and is based on ethylene oxide and/or propylene oxide.

9. The cosmetic preparation of claim 2, wherein the graft copolymer has a number average molecular weight of from 1000 to 30,000 g/mol.

10. The food product of claim 3, wherein the polyalkylene oxide has a number average molecular weight of from 300 to 100,000 and is based on ethylene oxide, propylene oxide and/or butylene oxide.

11. The food product of claim 3, wherein the polyalkylene oxide has a number average molecular weight of from 500 to 20,000 and is based on ethylene oxide and/or propylene oxide.

12. The food product of claim 3, wherein the graft copolymer has a number average molecular weight of from 1000 to 30,000 g/mol.

* * * * *